United States Patent [19]

Mahieu et al.

[11] Patent Number: 4,673,571
[45] Date of Patent: Jun. 16, 1987

[54] COSMETIC COMPOSITIONS FOR HAIR AND SKIN WHICH CONTAIN A METHACRYLIC OR ACRYLIC ACID COPOLYMER, AN ALKYL ACRYLATE AND/OR METHACRYLATE AND AN ALLYL DERIVATIVE

[75] Inventors: Claude Mahieu, Paris; Christos Papantoniou, Montmorency, both of France

[73] Assignee: Societe Anonyme dite: L'Oreal, France

[21] Appl. No.: 633,421

[22] Filed: Jul. 23, 1984

[30] Foreign Application Priority Data

Jul. 25, 1983 [FR] France .................. 83 12257

[51] Int. Cl.$^4$ .............. A61K 7/021; A61K 7/06; A61K 7/11; A61K 7/32
[52] U.S. Cl. .................. 424/70; 8/127.51; 8/405; 8/406; 424/DIG. 1; 424/DIG. 2; 424/DIG. 4; 424/DIG. 5; 424/59; 424/60; 424/63; 424/64; 424/65; 424/72; 424/73; 424/78; 424/80
[58] Field of Search ............ 424/59, DIG. 1, DIG. 2, 424/DIG. 4, 78, 80, 70

[56] References Cited

U.S. PATENT DOCUMENTS 3,884,964 5/1975 Otrhalek et al. ............ 260/486
3,966,404 6/1976 Papantoniou ............ 424/47
4,445,521 5/1984 Grollier et al. ............ 424/80

FOREIGN PATENT DOCUMENTS 2452032 5/1976 Fed. Rep. of Germany ........ 424/70
2265781 10/1975 France ............ 424/70

*Primary Examiner*—Dale R. Ore
*Attorney, Agent, or Firm*—Parkhurst & Oliff

[57] ABSTRACT

A cosmetic composition contained in a suitable carrier comprising at least one copolymer of acrylic or methacrylic acid, an alkyl acrylate and/or methacrylate and an allyl derivative having repetitive units which correspond to the following formulae:

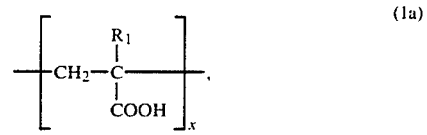

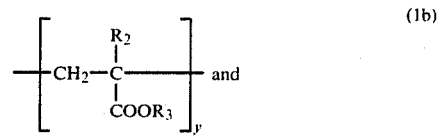

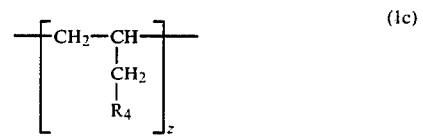

wherein:
$R_1$ and $R_2$ constitute a hydrogen atom or a methyl radical,
$R_3$ constitutes a linear or branched-chain alkyl radical having from 1 to 20 carbon atoms,
$R_4$ constitutes —OH, —NHCONH$_2$, or —OCOR$_5$,
$R_5$ constitutes a linear or branched-chain alkyl radical having from 1 to 5 carbon atoms,
x constitutes 40 to 90 weight percent,
y constitutes 8 to 50 weight percent,
z constitutes 2 to 25 weight percent, and the sum of x+y+z is from 80 to 100 weight percent.

The cosmetic composition is especially useful as a composition for the hair and skin.

12 Claims, No Drawings

COSMETIC COMPOSITIONS FOR HAIR AND SKIN WHICH CONTAIN A METHACRYLIC OR ACRYLIC ACID COPOLYMER, AN ALKYL ACRYLATE AND/OR METHACRYLATE AND AN ALLYL DERIVATIVE

SUMMARY OF THE INVENTION

The present invention pertains to new cosmetic compounds made with a methacrylic or acrylic acid copolymer, an alkyl acrylate and/or methacrylate and an allyl derivative. The compounds of the present invention are especially useful for the hair and skin. The above-mentioned polymers make it possible to supply properties which are especially sought after in cosmetics.

In compositions for hair, the polymers make it possible to obtain more body and more hold without observing non-cosmetic phenomena such as powdery, sticky or rough hair. They also facilitate the untangling and increase the shine of hair.

When the polymers are present in compositions for skin, they make the skin smoother and softer to the touch while increasing the texture of the compositions.

DETAILED DESCRIPTION

The present invention, a new industrial product, pertains to a cosmetic composition which contains in a suitable cosmetic carrier, at least one copolymer comprising recurring units derived from acrylic or methacrylic acid, an alkyl acrylate and/or methacrylate and an allyl derivative. The above-mentioned recurring units are represented by the following formulae:

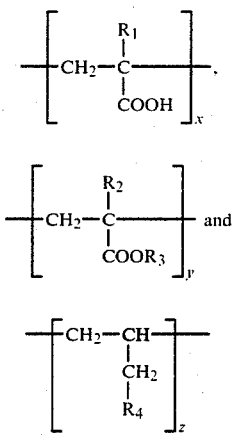

wherein:
$R_1$ and $R_2$ represent a hydrogen atom or a methyl group,
$R_3$ represents a linear or branched chain alkyl group having 1 to 10 carbon atoms,
$R_4$ represents —OH, —NHCONH$_2$, or —OCOR$_5$,
$R_5$ represents a linear or branched chain alkyl group having 1 to 5 carbon atoms,
x represents 40 to 90 weight percent,
y represents 8 to 50 weight percent,
z represents 2 to 25 weight percent, and the sum x+y+z equals betwen 80 and 100 weight percent.

The above-defined copolymers of the compositions according to the present invention have a molecular weight of from 5,000 to 200,000 and preferably have a molecular weight of from 10,000 to 50,000 as measured by the light diffusion method.

The recurring units of formula (1a) are derived from acrylic or methacrylic acid.

The recurring units of formula (1b) are derived from a lower alkyl acrylate and/or methacrylate, especially methyl, ethyl, propyl, isopropyl, butyl, hexyl, 2-ethyl hexyl or octyl acrylate or methacrylate.

The recurring units of formula (1c) are derived from allyl alcohol, allyl acetate, allyl propionate or allyl-urea.

According to a preferred embodiment, the copolymers comprise:
50 to 85 weight percent of the recurring units of formula (1a),
10 to 35 weight percent of the recurring units of formula (1b),
5 to 15 weight percent of the recurring units of formula (1c), When the above-defined sum x+y+z is less than 100 weight percent the remainder comprises recurring units of undetermined structure.

The copolymers of the compositions according to the present invention, include recurring units derived from polymerization of:
acrylic acid, methyl acrylate and allyl alcohol,
acrylic acid, methyl methacrylate and allyl alcohol,
acrylic acid, methyl acrylate, methyl methacrylate and allyl alcohol,
methacrylic acid, methyl methacrylate and allyl alcohol,
methacrylic acid, methyl acrylate and allyl alcohol,
acrylic acid, ethyl acrylate and allyl alcohol,
methacrylic acid, ethyl methacrylate and allyl alcohol,
acrylic acid, isopropyl acrylate and allyl alcohol,
methacrylic acid, ethyl methacrylate and allyl acetate,
acrylic acid, ethyl acrylate and allyl-urea.

The copolymer-free acid groups can be partially of completely neutralized with an inorganic base so as to improve solubility.

According to the present invention, the copolymers can advantageously be neutralized with an organic base in a quantity equal to about 10 to 150% and preferably 50 to 120% of the amount necessary for stoichiometric neutralization. The organic bases include monoethanolamine, diethanolomine, tri-ethanolamine, isopropanolamine, morpholine as well as some amino-alcohols such as 2-amino 2-methyl 1-propanol and 2-amino 2-methyl 1,3-propanediol.

In cosmetic compositions according to the present invention, the copolymers as defined above are present either as a main active ingredient or as an additive. The cosmetic compositions can be aqueous solutions, hydroalcoholic solutions (the alcohol being especially a lower alcohol such as ethanol or isopropanol), emulsions, creams, milks, gels, and they can be conditioned into sprays which contain a propellant such as nitrogen, nitrogen dioxide or fluorochlorinated hydrocarbons of the "freon" type.

Generally the polymer concentration in the cosmetic compositions according to the invention is between 0.1 and 30 weight percent and preferably between 0.5 and 0 weight percent.

In cosmetic compositions for hair, the polymers facilitate the rising hairdos and they give dry hair nervous qualities, a shiny aspect and make the hair easy to untangle.

The polymers can be present in cosmetic compositions for hair, either as additives or as main active ingredients, in setting lotions, treating compositions, combing lotions, combing creams or gels, or as additives in shampoo, setting, and permanent compositions, as well as compositions for dyeing, dye removing, restructuring lotion, anti-seborrhea treating lotion or lacquer for hair.

The lotions are aqueous or hydro-alcoholic lotions in which the pH is close to neutrality and can range from 5 to 8.

The treating creams are made with a support that is a soap-based or fatty alcohol-based formula in the presence of an emulsifier. The soaps can be made from natural fatty or synthetic acids having from 12 to 20 carbon atoms (such as lauric acid, myristic acid, palmitic acid, oleic acid, ricinoleic acid, stearic acid, isostearic acid and their mixtures) in concentrations of from 10 to 30% and alkalinizing agents (such as sodium, potassium, ammonia, monoethanolamine, triethanolamine and their mixtures).

The treating gels contain thickening agents such as sodium alginate or arabic gum or cellulose derivatives optionally in the presence of a solvent. The thickening agent concentration ranges from 0.5 to 30 weight percent and preferably ranges from 0.5 to 15 weight percent.

The solvents used can be aliphatic lower alcohols, glycols and their ethers with the concentration of the solvents ranging from 2 to 20%.

According to a preferred embodiment, the compositions are used in the form of shampoos, and are characterized by the fact that they contain at least one of the above-defined polymers and at least one cationic, non-ionic, anionic, amphoteric detergent or their mixture.

The compositions in the form of shampoos can also contain various ingredients, such as perfumes, coloring agents, preservatives, thickening agents, foam stabilizing agents, and softening agents. In the shampoos the detergent concentration is usually between 3 and 50 weight percent and the polymer concentration is preferably between 0.1 and 4 weight percent.

The compositions according to the present invention can also be used as setting lotions or brushing lotions and are characterized by the fact that they include at least one of the above-defined polymers in an aqueous or hydro-alcoholic solution.

The compositions according to the present invention can also be applied before or after shampooing or between shampooings as a formulae for hair treatment.

The compositions can also contain at least one cosmetic resin with anionic or cationic features. Cosmetic resins which can be used in such lotions are known and described in cosmetology works.

The compositions according to the present invention can also be used as dyeing compositions for hair, and are characterized by the fact that they contain at least one of the above-defined polymers and at least one coloring agent for hair and a support.

The dyeing compositions are preferably gellable liquids. They contain in addition to the polymer, a coloring agent or coloring precursor, either non-ionic polyoxyethylene or polyglycerol derivatives and solvents, or liquid fatty acid soaps such as those of oleic or isostearic acid and solvents. The soaps are sodium, potassium, ammonia or mono-, di-or tri-ethanolamine soaps.

The compositions according to the present invention which are designed for skin treatment are preferably employed as creams, milks, emulsions, gels or aqueous or hydro-alcoholic solutions. The polymer concentration in these compositions ranges from 0.1 to 10 weight percent and preferably ranges from 0.25 to 5 weight percent. The ingredients which are usually present in these compositions include perfumes, coloring agents, pigments, preserving agents, thickening agents, sequestering agents, emulsifying agents, sun filters, fillers, stabilizing agents and skin softening agents. These compositions render the skin smooth and give it a softness that is pleasant to touch.

The skin compositions of the present invention represent treatment creams or lotions for the hands or the face, sunscreen creams, tinted creams, make-up removal milks, foamy liquids for baths, after shave lotions, "eau de toilette", shaving foam, pencils for blush, pencils that may be colored especially for lips, for make-up or for body hygiene or for deodorant compositions.

The above-defined polymers can be present in the compositions for skin treatment either as additives or as main active ingredients.

The skin compositions can also contain various active substances such as humectant agents and healing agents and can be displayed as aqueous or hydro-alcoholic solutions, creams, milks, etc.

The copolymers, some of which are described in U.S. Pat. No. 3,884,964, can be obtained according to standard polymerization methods i.e by polymerization in solution in a solvent, in mass or eventually in emulsion.

The polymerization process in solution is usually achieved in an inert solvent like ethyl acetate.

The polymerization initiators which can be used in this polymerization process are preferably azobisisobutyronitrile, peresters, percarbonates, or oxido-reduction systems. The polymerization initiator can be used either alone or as a mixture.

The amount of the polymerization initiator is usually from 0.1 to 6 weight percent in relation to the overall weight of the monomers to be copolymerized.

The polymerization reaction is preferably carried out at a temperature of from 45 to 100° C. and is carried out especially at the reflux temperature of the reacting mixture.

The reaction time is preferably from 2 to 24 hours. Another especially advantageous method can be used to obtain polymers in which the above-defined $R_1$ and $R_2$ radicals are identical, or they represent either a hydrogen atom or a methyl radical.

Indeed, in this particular instance, the polymerization reaction can be achieved in an alcohol solution which might partially esterify the carboxylic acid functions of the starting acrylic or methacrylic acid.

This method is especially preferred when the above-defined $R_3$ radical of recurring units from formula (1b) constitutes a lower alkyl group having from 1 to 3 carbon atoms.

According to this method, the polymerization reaction is carried out with acrylic or methacyrlic acid precursors and at least one monomer which will yield the recurring units of formula (lc).

During the polymerization reaction, the acid functions of the acrylic or methacrylic acid are partially esterifed by the lower aliphatic alcohol used as a solvent.

According to this method, it is thus possible to esterify about 20% of the acid functions of the starting acrylic or methacrylic acids.

In this method, the polymerization initiators are those that are commonly used such as organic compounds of the peroxide, perester or percarbonate category but are preferably azobisisobutyronitrile or oxido-reduction systems.

By manipulating specific operating condition parameters, it is possible to adjust the molecular weight of the desired copolymers. The specific operating condition parameters are, the amount of the polymerization initiator and the concentration of monomers in the reacting solvent.

According to a preferred embodiment, when it is desired to obtain polymers having a molecular weight of from 10,000 to 50,000, the method involves copolymerizing acrylic or methacrylic acid and the monomer which yields the recurring units of formula (lc) in a solution of an aliphatic alcohol which might partially esterify the recurring units of formula (1a), in the presence of hydrogen peroxide and an acceleration factor which forms free radicals. This acceleration factor can be UV radiation or an inorganic or organic compound with reducing properties. The inorganic or organic compounds with reducing properties include ferrous chloride, copper chloride and ascorbic acid.

If it is desired to obtain a more significant esterification rate of the recurring units of formula (1a), the copolymerization reaction must be performed in the presence of a strong acid such as sulfuric acid or paratoluene sulfonic acid.

The following examples of copolymer preparations and cosmetic compositions are provided in order to better understand the invention and to serve as a non-limiting illustration.

EXAMPLE 1

A preparation of polymer was made containing 68% acrylic acid, 8% ethyl acrylate and 12% allyl alcohol with the remainder being comprised of recurring units of undetermined structure.

320 g of acrylic acid, 800 ml of ethanol, 80 g of allyl alcohol, and 60 g of a 30% solution of hydrogen peroxide was introduced in a 2 liter reactor equipped with a stirrer, a coolant, a nitrogen inlet and a tube to introduce reagents.

The mixture was then heated to 80° C. When this temperature was attained, the heating was stopped and a dispersion of 400 mg of copper chloride in 400 ml of water was added to the mixture. As soon as the first drops of the copper chloride dispersion were added, the temperature of the reacting environment was raised to 83° C. and then a strong reflux of ethanol was observed. Then the addition rate of the copper chloride dispersion was adjusted so that it became complete in 40 minutes by heating it so as to maintain the reflux flow of solvent.

Afterwards, the polymerization reaction was continued with the reflux of solvent for about 2½ hours.

After cooling, the reaction mixture was concentrated by one-half in a rotating evaporator, then it was poured into plates and dried in an oven at 50° C. under $26.10^2$ Pa.

Analyses:
Acid index: 532
Viscosity of solution at 50% of polymer in water at 25° C.: 217cPo.

The ester and alcohol content were determined by proton NMR.

EXAMPLE 2

A preparation of polymer was made containing 64% acrylic acid, 8% ethyl acrylate and 12% allyl alcohol with the remainder being comprised of recurring units of undetermined structure.

320 g of acrylic acid, 800 ml of ethanol, 80 g of allyl alcohol, 60 g of a 30% solution of hydrogen peroxide was introduced in a 2 liter reactor equipped with a stirrer, a coolant, a nitrogen inlet and a tube for inserting reagents.

Then the mixture was heated to a temperature of 80° C. When this temperature was attained, the heating was stopped and a solution of 20 g of ascorbic acid in 40 ml of water was added to the mixture.

As soon as the first drops of the solution were added the temperature of the reacting enviroment was raised to 86° C. and a strong reflux of ethanol was observed. Then the addition rate of the solution was adjusted so that it became complete after 40 minutes with heating to maintain the reflux of solvent. Afterwards, the polymerization reaction was continued at the reflux temperature of solvent for about 2½ hours.

After cooling, the reaction mixture was diluted with 1500 g of ethyl cellosolve, and was then concentrated to 1200 g in order to remove all of the water, ethanol, and residual allyl alcohol. The polymer solution was then poured into 15 liters of an acetone-oil ester mixture (60/40) under strong stirring. The recovered polymer was dried at 50° C. under $26.10^2$Pa.

Analyses:
Acid index: 497
Viscosity of a 50% polymer solution in water at 25° C.: 740cPo.

The ester and alcohol content were determined by proton NMR.

EXAMPLE 3

A preparation of polymer was made containing 62% acrylic acid, 8% methyl acrylate and 13% allyl acetate with the remainder being comprised of recurring units of undetermined structure.

297.5 g of acrylic acid, 127.5 g of allyl acetate, 2,518 g of methanol and 40 g of a 30% solution of hydrogen peroxide was introduced in a 4 liter reactor equipped with a quartz plunger pipe which contained a UV Q 2020 2000W lamp from the ORIGINAL HANAU company, a West German Company. This solution, which was stirred and maintained under nitrogen, was then irradiated for 2 hours while keeping the temperature at 50° C.

The analysis of the reaction mixture demonstrated that the acrylic acid was totally consumed.

The reaction mixture was then concentrated to 1000 g and then was added to 20 liters of sulfuric ether under strong stirring. Then, the polymer was dried in an oven at 50° C.

Analyses:
Acid index: 487
Viscosity of a 50% solution in water at 25° C.: 265cPo.

EXAMPLE 4

A preparation of polymer was made containing 70% acrylic acid, 9% methyl acrylate and 20% N-allyl-urea with the remainder being commmprised of recurring units of undetermined structure.

According to a process analogous to that of Example 3, 160 g of acrylic acid, 40 g of N-allyl-urea, 2240 g of methanol, and 40 g of 30% solution of hydrogen peroxide was added to the same kind of reactor as described in Example 3.

The polymerization reaction was continued for 4½ hours at 50° C., which is the time period necessary for complete consumption of the acrylic acid.

The reaction mixture was concentrated to 1000 g and was then poured into 20 liters of sulfuric ether under strong stirring. The polymer was then dried in an oven in a vacuum.

Analyses:
Acid index: 547
Viscosity of a 50% solution in water at 25° C.: 97 cPo.
The methyl ester rate was determined by proton NMR.

The content of N-allyl-urea deduced from the percentage of nitrogen through micro-analysis was found to be 5.72%.

EXAMPLE 5

A preparation of a polymer was made containing 67% acrylic acid, 9% methyl acrylate and 12% allyl alcohol with the remainder being comprised of recurring units of undetermined structure.

According to a process analogous to that of example 3, 340 g of acrylic acid, 85 g of allyl alcohol, 2524 g of methanol and 40 g of a solution of hydrogen peroxide was added to the same kind of reactor as described in Example 3.

The polymerization reaction was continued for 2 hours at 50° C., which is the time necessary for complete consumption of the acrylic acid.

The reaction mixture was concentrated to 1000 g and was then poured in 20 liters of sulfuric ether under strong stirring. The polymer was then dried in an oven at 50° C.

Analyses:
Acid index: 519
Viscosity of a 50% solution in water at 25° C.: 303cPo.
The methyl ester content was determined by proton NMR.

EXAMPLE 6

A preparation of a polymer was made containing 56% acrylic acid, 17% ethyl acrylate and 11% allyl alcohol with the remainder being comprised of recurring units of undetermined structure.

160 g of acrylic acid, 40 g of allyl alcohol, 600 g of ethanol and 4 g of azobisisobutyronitrile were added to a 3 liter reactor equipped with a nitrogen inlet. The reaction mixture was brought to the reflux temperature of ethanol for 5 hours. Then, 1 g of azobisisobutyronitril in a solution of 10 g of ethanol and 100 g of heptane was added to the reactor. Then 300 g of the solvent was distilled off to remove the unpolymerized allyl alcohol.

The reaction mixture then contained less than 2% residual acrylic acid and the polymer was obtained by pouring the raw solution into 10 liters of sulfuric ether with stirring. The polymer was dried in an oven at 50° C.

Analyses:
Acid index: 435
Viscosity of a 50% solution in water at 25° C.: 1670cPo.

EXAMPLE 7

A preparation of a polymer was made containing 53% acrylic acid, 8% methyl acrylate, 22% methyl methacrylate and 9% allyl alcohol with the remainder being comprised of recurring units of undetermined structure.

120 g of acrylic acid, 40 g of methyl methacrylate, 40 g of allyl alcohol, 720 ml of methanol and 30 g of a 30% hydrogen peroxide solution was added to a 2 liter reactor equipped with a stirrer, a coolant, a nitrogen inlet and a tube for inserting reagents.

The mixture was brought to a temperature of 80° C. and then after the heating was stopped, a solution of 10 g of ascorbic acid in water was added for 40 minutes. The polymerization reaction was continued at the reflux temperature of solvent for 2½ hours. After cooling, the mixture was concentrated to ⅔ in a rotating evaporator and was then poured drop by drop into 8 liters of acetonitrile under strong stirring. The polymer obtained was dried in an oven at 50° C.

Analyses:
Acid index: 413
Viscosity of a 50% solution in ethanol at 25° C.: 1400cPo.

The ester and alcohol contents were determined by proton NMR (solvent DMSO).

EXAMPLES OF COMPOSITIONS

EXAMPLE A

A setting lotion was prepared by mixing the following ingredients:

| | |
|---|---|
| polymer prepared according to example 1 | 2 g. |
| sodium hydroxyde q.s.p. | pH 7 |
| water q.s.p. | 100 g. |

In this example the polymer of example 1 can be replaced with that of example 5.

EXAMPLE B

A shampoo composition was prepared by mixing the following ingredients:

| | |
|---|---|
| triethanolamine lauryl sulfate | 10 g. |
| polymer prepared according to example 2 | 1 g. |
| sodium hydroxyde q.s.p. | pH 7 |
| water q.s.p. | 100 g. |

In this example the polymer of example 2 can be replaced with that of example 6.

EXAMPLE C

A shampoo composition was prepared by mixing the following ingredients:

| | |
|---|---|
| Lauric alcohol polyglycerolated with 4 moles of glycerol | 10 g. |
| polymer prepared according to example 1 | 2 g. |
| sodium hydroxyde q.s.p. | pH 7 |
| water q.s.p. | 100 g. |

In this example the polymer of example 1 can be replaced with that of example 3.

EXAMPLE D

A beauty mask was prepared by mixing the following ingredients:

| | |
|---|---|
| polymer prepared according to example 2 | 15 g. |

-continued

| | |
|---|---|
| 2-amino 2-methyl 1-propanol q.s.p. | pH 7 |
| propylene glycol | 5 g. |
| 4-hydroxymethyl benzoate | 0.2 g. |
| ethanol | 15 g. |
| kaolin | 10 g. |
| titanium dioxide | 0.5 g. |
| triethanolamine lauryl sulfate | 0.6 g. |
| perfume | 0.15 g. |
| sterile deionized water q.s.p. | 100 g. |

In this example the polymer of example 2 can be replaced with that of example 4 or example 7.

What is claimed is:

1. A cosmetic composition for hair, comprising an aqueous or hydroalcoholic solution of an alcohol selected from the group consisting of ethanol and isopropanol and from 0.1 to 30 weight percent of a copolymer comprising repetitive units derived from (1a) an acrylic or methacrylic acid, at least one of (1b) a lower alkyl acrylate and methacrylate and (1c) an allyl derivative, said recurring units being represented by the following formulae:

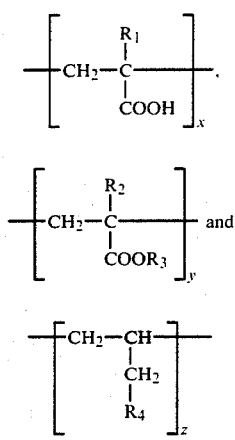

wherein:
$R_1$ and $R_2$ are selected from the group consisting of hydrogen and methyl radicals;
$R_3$ represents a linear or branched chain alkyl radical having from 1 to 10 carbon atoms;
$R_4$ is selected from the group consisting of —OH, —NHCONH$_2$ and —OCOR$_5$;
$R_5$ represents a linear or branched chain alkyl radical having from 1 to 5 carbon atoms; and
x represents 40 to 90 weight percent;
y represents 8 to 50 weight percent;
z represents 1 to 15 weight percent; and
the sum of x+y+z is from 80 to 100 weight percent, said copolymer having a molecular weight of from 5,000 to 200,000 as measured by the light diffusion method.

2. The composition of claim 1, wherein said copolymer has a molecular weight of from 10,000 to 50,000.

3. The composition of claim 1, wherein said recurring units of formula (1b) of said copolymer are derived from a lower alkyl acrylate selected from the group consisting of methyl acrylate, ethyl acrylate, propyl acrylate, isopropyl acrylate, butyl acrylate, hexyl acrylate, 2-ethyl hexyl acrylate, octyl acrylate and methacrylate thereof.

4. The composition of claim 1, wherein said recurring units of formula (1c) of said copolymer are derived from the goup consisting of allyl alcohol, allyl acetate, allyl propionate and allyl-urea.

5. The composition of claim 1, wherein x represents from 50 to 85 weight percent, y represents from 10 to 35 weight percent and z represents from 5 to 15 weight percent.

6. The composition of claim 1, wherein said copolymer comprises recurring units derived from the group consisting of:
(a) acrylic acid, methyl acrylate and allyl alcohol;
(b) acrylic acid, methyl methacrylate and allyl alcohol;
(c) acrylic acid, methyl acrylate, methyl methacrylate and allyl alcohol;
(d) methacrylic acid, methyl methacrylate and allyl alcohol;
(e) methacrylic acid, methyl acrylate and allyl alcohol;
(f) acrylic acid, ethyl acrylate and allyl alcohol;
(g) methacrylic acid, ethyl methacrylate and allyl alcohol;
(h) acrylic acid, isopropyl acrylate and allyl alcohol;
(i) methacrylic acid, ethyl methacrylate and allyl acetate; and
(j) acrylic acid, ethyl acrylate and allyl-urea.

7. The composition of claim 1, wherein free acid groups contained in said copolymer are neutralized with a base.

8. The composition of claim 7, wherein said base is an organic base selected from the group consisting of monoethanolamine, diethanolamine, triethanolamine, isopropanolamine, morpholine, 2-amino 2-methyl 1-propanol and 2-amino 2-methyl 1,3-propanediol.

9. The composition of claim 1, wherein said copolymer is present at a concentration of from 0.5 to 10 weight percent.

10. The composition of claim 1, wherein said composition has a pH of 5 from 8.

11. The composition of claim 1, further comprising a detergent selected from the group consisting of cationic, nonionic, anionic, and amphoteric detergents or a mixture thereof wherein said composition comprises a shampoo.

12. The composition of claim 11, wherein said detergent is present at a concentration of from 3 to 50 weight percent.

* * * * *